United States Patent
Persidis et al.

(10) Patent No.: US 9,795,601 B2
(45) Date of Patent: Oct. 24, 2017

(54) COMPOSITIONS AND METHODS FOR CANCER TREATMENT

(75) Inventors: Andreas Persidis, Athens (GR); Spyros Deftereos, Athens (GR)

(73) Assignee: BIOVISTA, INC., Charlottesville, VA (US)

( * ) Notice: Subject to any disclaimer, the term of this patent is extended or adjusted under 35 U.S.C. 154(b) by 487 days.

(21) Appl. No.: 13/993,741

(22) PCT Filed: Dec. 15, 2011

(86) PCT No.: PCT/US2011/065085
§ 371 (c)(1),
(2), (4) Date: Jun. 13, 2013

(87) PCT Pub. No.: WO2012/082992
PCT Pub. Date: Jun. 21, 2012

(65) Prior Publication Data
US 2013/0259800 A1   Oct. 3, 2013

Related U.S. Application Data

(60) Provisional application No. 61/423,267, filed on Dec. 15, 2010.

(51) Int. Cl.
| | | |
|---|---|---|
| *A61K 31/422* | (2006.01) | |
| *A61K 31/42* | (2006.01) | |
| *C07D 263/20* | (2006.01) | |
| *A61K 31/496* | (2006.01) | |
| *A61K 31/4439* | (2006.01) | |
| *A61K 31/495* | (2006.01) | |
| *A61K 31/5377* | (2006.01) | |
| *A61K 31/655* | (2006.01) | |
| *A61K 31/704* | (2006.01) | |
| *A61N 5/10* | (2006.01) | |

(52) U.S. Cl.
CPC ............ *A61K 31/496* (2013.01); *A61K 31/42* (2013.01); *A61K 31/4439* (2013.01); *A61K 31/495* (2013.01); *A61K 31/5377* (2013.01); *A61K 31/655* (2013.01); *A61K 31/704* (2013.01); *A61N 5/1001* (2013.01); *A61N 5/1077* (2013.01); *C07D 263/20* (2013.01)

(58) Field of Classification Search
None
See application file for complete search history.

(56) References Cited

U.S. PATENT DOCUMENTS

| | | | | |
|---|---|---|---|---|
| 7,550,143 | B2 * | 6/2009 | Chang | B82Y 5/00 424/134.1 |
| 2002/0016301 | A1 * | 2/2002 | Godek | A61K 31/7048 514/28 |
| 2005/0014729 | A1 * | 1/2005 | Pulaski | A61K 31/00 514/165 |
| 2005/0171032 | A1 * | 8/2005 | Solomon | A61K 31/225 514/28 |
| 2007/0149452 | A1 * | 6/2007 | Marshall | 514/12 |
| 2008/0176828 | A1 * | 7/2008 | Williams | A61K 31/16 514/210.06 |

OTHER PUBLICATIONS

Roberts et al. J Pineal Res, 28, p. 165-171, 2000.*
Ruegg et al. Annals of Medicine, 35, p. 476-487, 2003.*

* cited by examiner

*Primary Examiner* — Nissa Westerberg
(74) *Attorney, Agent, or Firm* — Brannon Sowers & Cracraft PC

(57) ABSTRACT

The invention described herein pertains to the use of oxazolidinone antibiotics, alone or in combination, in the treatment of cancer. In particular, the invention pertains to the treatment of malignant gliomas, thyroid cancer or melanoma, or borderline forms of malignant glioma, thyroid cancer or melanoma.

17 Claims, No Drawings

COMPOSITIONS AND METHODS FOR CANCER TREATMENT

CROSS-REFERENCE TO RELATED APPLICATIONS

This application is a U.S. national application under 35 U.S.C. §371(b) of International Application Serial No. PCT/US2011/065085 filed Dec. 15, 2011, which claims priority under 35 USC §119(e) to U.S. Provisional Application Ser. No. 61/423,267 filed on Dec. 15, 2010, the entire disclosures of which are incorporated herein by reference.

TECHNICAL FIELD

The invention described herein pertains to the use of oxazolidinone antibiotics, alone or in combination, in the treatment of cancer. In particular, the invention pertains to the treatment of malignant gliomas, thyroid cancer or melanoma, or borderline forms of malignant glioma, thyroid cancer or melanoma.

BACKGROUND AND SUMMARY OF THE INVENTION

Cancers, or malignant neoplasms, include a large group of different diseases, all of which involve at least in part unregulated cell growth. In cancer, cells divide and grow uncontrollably, forming malignant tumors. The malignant tissue may invade nearby tissues, or spread to more distant parts of the body through the lymphatic system or bloodstream. Cell division is a complex process that is normally tightly regulated, and generally, healthy cells control their own growth and will destroy themselves if growth becomes sufficiently dysregulated. Some cancers occurs when problems in the genes of a cell prevent these controls from functioning properly. These problems may come from damage to the gene or may be inherited, and can be caused by various sources inside or outside of the cell. Faults in two types of genes are especially important: oncogenes, which drive the growth of cancer cells, and tumor suppressor genes, which prevent cancer from developing.

Cancer is usually treated with chemotherapy, radiation therapy and surgery. The chances of surviving the disease vary greatly depending upon the type and location of the cancer and the extent of disease at the start of treatment. While cancer can affect people of all ages, and a few types of cancer are more common in children, the risk of developing cancer generally increases with age. In 2007, cancer caused about 13% of all human deaths worldwide (7.9 million).

Depending upon the tissue or tumor type, cancers may be categorized. For example, carcinomas are generally cancers derived from epithelial cells. This group includes many of the most common cancers, particularly in the aged, and include nearly all those developing in the breast, prostate, lung, pancreas, and colon. Sarcomas are generally cancers arising from connective tissue, such as bone, cartilage, fat, and nerve tissue, each of which develop from cells originating in mesenchymal cells outside the bone marrow. Lymphomas and leukemias include two classes of cancers that arise from hematopoietic (blood-forming) cells that leave the marrow and tend to mature in the lymph nodes and blood, respectively. Germ cell tumors are generally cancers derived from pluripotent cells, most often presenting in the testicle or the ovary. Blastomas are generally cancers derived from immature "precursor" cells or embryonic tissue, and may occur more commonly in children.

Malignant gliomas are highly invasive and neurologically destructive tumors, the most aggressive manifestation of which is glioblastoma. The term glioma encompasses a group of cancers that includes astrocytomas, oligodendrogliomas, oligoastrocytomas, and ependymomas. The most widely used scheme for classification and grading of glioma is that of the World Health Organization, where gliomas are classified according to their hypothesized line of differentiation, such as whether they display features of astrocytic, oligodendrial or ependymal cells. They are graded on a scale of I to IV according to their degree of malignancies. For example, glioblastoma (GBM) is classified as grade IV anaplastic astrocytoma.

Glioblastoma is the most common primary brain tumor in adults. More than half of the 18,000 patients diagnosed with malignant primary brain tumors in US each year have GBM. GBM is an anaplastic, highly cellular tumor, with high proliferation indices, microvascular proliferation and focal necrosis. Signs and symptoms depend on several factors, including size, rate of growth, and localization of the tumor within the brain, and are mainly represented by headache, seizures, neurological deficits, and changes in mental status. GBM prognosis remains pessimistic. Survival time is less than 2 years for the majority of patients. Karnofsky performance status (KPS) is one of the most important prognostic factors. For example, patients with KPS>70 are alive at 18 months in approx 18% of cases, compared with 13% of patients with lower KPS scores. Primary GBM develops de novo from glial cells, typically has a clinical history of less than six months, is more common in older patients and presents small-cell histology. Secondary GBM develops over months or years from pre-existing low-grade astrocytomas, predominantly affects younger people and presents giant-cell histology. Current therapies in both neoadjuvant or adjuvant therapy have been reported to prolong disease-free survival but not overall survival.

Melanoma, is a malignant neoplasm of melanocytes and is reportedly the most deadly form of skin cancer (Chudnovsky et al., 2005). The incidence of melanoma has been reported to continue to increase despite public health initiatives to promote protection against harmful effects of the sun. In Europe, approximately 26,100 males and 33,300 females are diagnosed each year with melanoma, and about 8,300 males and 7,600 females die from the disease. It is the eighth most commonly diagnosed cancer in females and seventeenth in males. Light skin type, large numbers of nevi and excessive sun exposure, mainly in childhood, are reportedly the major modifiers of melanoma risk (Houghon and Polsky, 2002). When melanoma is detected in its early stages it is curable, but once advanced it becomes more difficult to treat. The primary lesions are located in limbs (22%), trunk (40%), head and neck (15%), and 16% in other sites (Capizzi and Donohue, 1994). The most common sites of metastases found in the autopsy are skin and subcutaneous tissue (75%), lung (70%), liver (68%), small intestine (58%), pancreas (53%), heart (49%), brain (39%), and spleen (36%). With visceral metastasis, the 5-year survival drops to approximately 6%, and the median survival from time of diagnosis is 7.5 months (Barth et al, 1995).

Thyroid cancer generally refers to any of five kinds of malignant tumors of the thyroid gland: papillary, follicular, hurthle cell, medullary, and anaplastic. Papillary and follicular, and hurthle cell tumors are the most common. They grow slowly, and may recur, but are generally not fatal in patients under 45 years of age. Medullary tumors have a good prognosis if restricted to the thyroid gland, but a poorer prognosis if metastasis occurs. Anaplastic tumors are fast-growing and have thusfar responded poorly to all therapies.

Thyroid nodules are diagnosed by ultrasound guided fine needle aspiration (USG/FNA) or frequently by thyroidectomy (surgical removal and subsequent histological examination). Because thyroid cancer can take up iodine, radioactive iodine is commonly used to follow and treat thyroid carcinomas, followed by thyroid stimulating hormone (TSH) suppression using thyroxine therapy.

Thyroid cancer is the most common endocrine malignancy, with 33,500 new cases of thyroid cancers estimated to be diagnosed in the U.S. in 2008. Differentiated thyroid carcinoma comprises 90% of all cases. Once thyroid cancer metastasizes to distant sites and is no longer amenable to radioactive iodine therapy or surgery, expected survival declines rapidly. Currently, there is only one FDA-approved therapy for thyroid cancer.

The treatments of cancer, including malignant gliomas, melanoma, and thyroid cancers, represent unmet medical needs.

It has been discovered that oxazolidinone antibiotics, and pharmaceutically acceptable salts thereof, are useful in treating cancer, and in particular useful against malignant glioma, melanoma and thyroid cancer and are expected to be useful in treating patients suffering from or in need of relief from these cancers. The use of oxazolidinones, or pharmaceutically acceptable salts thereof, in treating cancers, including malignant gliomas, melanoma, and thyroid cancer has heretofore been unknown.

DETAILED DESCRIPTION

In one illustrative embodiment of the invention, there is provided a method for treating cancers, including malignant glioma, thyroid cancer, and melanoma, including borderline forms of malignant glioma, thyroid cancer, and melanoma. The methods described herein include administering to a patient in need thereof a therapeutically effective amount of one or more oxazolidinone antibiotics, according to any of the descriptions herein, and/or pharmaceutically acceptable salts thereof. Another embodiment described herein is the use of one or more oxazolidinone antibiotics, according to any of the descriptions herein, and/or pharmaceutically acceptable salts thereof, for treating cancers, including malignant glioma, thyroid cancer, and melanoma, including borderline forms of malignant glioma, thyroid cancer, and melanoma. A further embodiment described herein is the use of one or more oxazolidinone antibiotics, according to any of the descriptions herein, and/or pharmaceutically acceptable salts thereof, for the manufacture of a medicament for treating cancers, including malignant glioma, thyroid cancer, and melanoma, including borderline forms of malignant glioma, thyroid cancer, and melanoma. A further embodiment described herein are compositions comprising one or more oxazolidinone antibiotics, according to any of the descriptions herein, and/or pharmaceutically acceptable salts thereof, for treating cancers, including malignant glioma, thyroid cancer, and melanoma, including borderline forms of malignant glioma, thyroid cancer, and melanoma. A further embodiment described herein are unit doses and unit dosage forms comprising a therapeutically effective amount of one or more oxazolidinone antibiotics, according to any of the descriptions herein, and/or pharmaceutically acceptable salts thereof, for treating cancers, including malignant glioma, thyroid cancer, and melanoma, including borderline forms of malignant glioma, thyroid cancer, and melanoma. As used herein, the term "borderline form" of a cancer may include a form which some clinicians consider a precursor form of a cancer. It is to be understood herein that method, use, composition, and/or unit dose embodiments described herein that refer to cancer, including embodiments described herein that refer particularly to malignant glioma, thyroid cancer, and/or melanoma, include such borderline forms in each case.

In one embodiment for such a method, use, composition, or unit dose, the oxazolidinone antibiotic is a compound of the following formula (I)

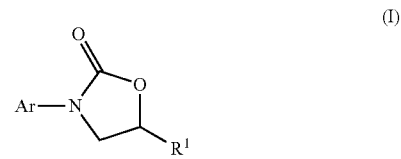

wherein Ar is an optionally substituted aryl or heteroaryl group and $R^1$ is an N-substituted amino(1-3C)alkyl group, a hydroxy(1-3C)alkyl group or a (5-membered-heteroaryl)oxy(1-3C)alkyl group. In one embodiment, the oxazolidinone antibiotic is a compound which falls within the scope of oxazolidinone antibiotic compounds generically or specifically disclosed in any of the above mentioned patents, each of which is individually incorporated herein by reference.

In another embodiment for such a method, use, composition, or unit dose, the oxazolidinone antibiotic is a compound of the following formula (II)

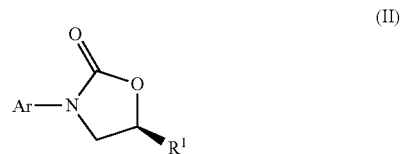

wherein Ar is an optionally substituted aryl or heteroaryl group and $R^1$ is an N-substituted amino(1-3C)alkyl group, a hydroxy(1-3C)alkyl group or a (5-membered-heteroaryl)oxy(1-3C)alkyl group. In one embodiment, the oxazolidinone antibiotic is a compound which falls within the scope of oxazolidinone antibiotic compounds generically or specifically disclosed in any of the above mentioned patents, each of which is individually incorporated herein by reference.

In another embodiment, for a compound of formula (I) or formula (II), Ar is a group

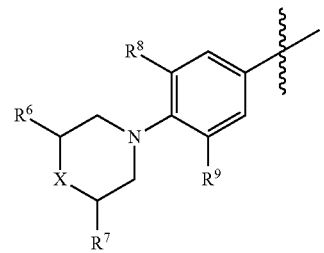

wherein X is O, S, SO, $SO_2$, $SNR^4$, $S(O)NR^4$, $NR^4$ or $NC(O)CH_2OR^4$, wherein $R^4$ is selected from hydrogen, $R^5$ and $C(O)R^5$ groups wherein $R^5$ is ($C_1$-$C_8$) hydrocarbyl optionally substituted with one or more hydroxy, fluorine or chlorine groups; $R^6$ and $R^7$ are independently selected from hydrogen, methyl and cyano groups; and $R^8$ and $R^9$ are independently selected from hydrogen, fluorine and chlorine atoms. In one embodiment, $R^6$ and $R^7$ are hydrogen, one of $R^8$ and $R^9$ is fluorine and the other of $R^8$ and $R^9$ is hydrogen.

For any of the above embodiments, for a compound of formula (I) or formula (II), an embodiment of $R^1$ is a group $(CH_2)_nN(R^2)COR^3$, a group $(CH_2)_nOH$ or a group $(CH_2)_nOR^{10}$ wherein n is 1, 2 or 3, and $R^2$ and $R^3$ are independently selected from hydrogen and ($C_1$-$C_8$) hydrocarbyl optionally substituted with one or more hydroxy, fluorine or chlorine groups and $R^{10}$ is a C-linked 5-membered heteroaryl ring containing 2 to 4 heteroatoms independently selected from N, O and S, which ring is optionally substituted on an available carbon atom by 1 or 2 substituents independently selected from ($C_1$-$C_4$) alkyl, amino, ($C_1$-$C_4$) alkylamino, ($C_1$-$C_4$) alkoxy and halo, and/or on an available nitrogen atom, provided the ring is not thereby quaternized, by ($C_1$-$C_4$) alkyl.

In one embodiment, the oxazolidinone antibiotic is (S)—N-[[3-[3-fluoro-4-(4-morpholinyl)phenyl-2-oxo-5-oxazolidinyl]methyl]acetamide (linezolid), N-[(5S)-[3-[[3-fluoro-4-[4-(2-fluoroethyl)-3-oxopiperazin-1-yl]phenyl]-2-oxooxazolidin-5-yl]methyl]acetamide, N-[[(5S)-3-[4-(1,1-dioxido-4-thiomorpholinyl)-3,5-difluorophenyl]-2-oxo-5-oxazolidinyl]methyl]acetamide, (S)—N-[[3-[5-(4-pyridyl)pyrid-2-yl]-2-oxo-5-oxazolidinyl]methyl]acetamide, or (S)—N-[[3-[5-(3-pyridyl)thiophen-2-yl]-2-oxo-5-oxazolidinyl]methyl]acetamide.

In one embodiment, the oxazolidinone antibiotic is N-[[(5S)-3-[4-(1,1-dioxido-4-thiomorpholinyl)-3,5-difluorophenyl]-2-oxo-5-oxazolidinyl]methyl]acetamide.

In one embodiment, the oxazolidinone antibiotic is a compound of the formula

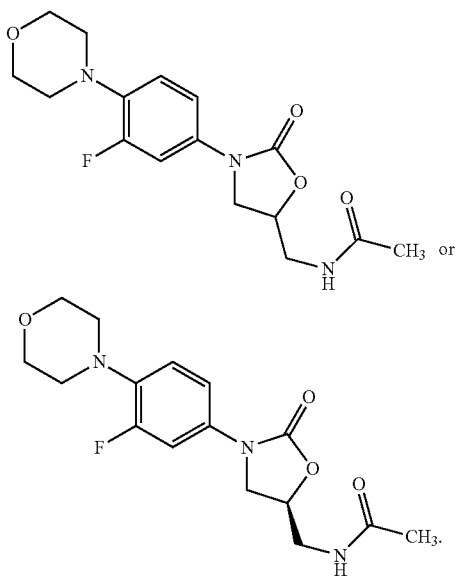

This embodiment includes (S)—N-[[3-[3-fluoro-4-(4-morpholinyl)phenyl-2-oxo-5-oxazolidinyl]methyl]acetamide, also known as linezolid.

In another embodiment, the oxazolidinone antibiotic is a compound of the formula

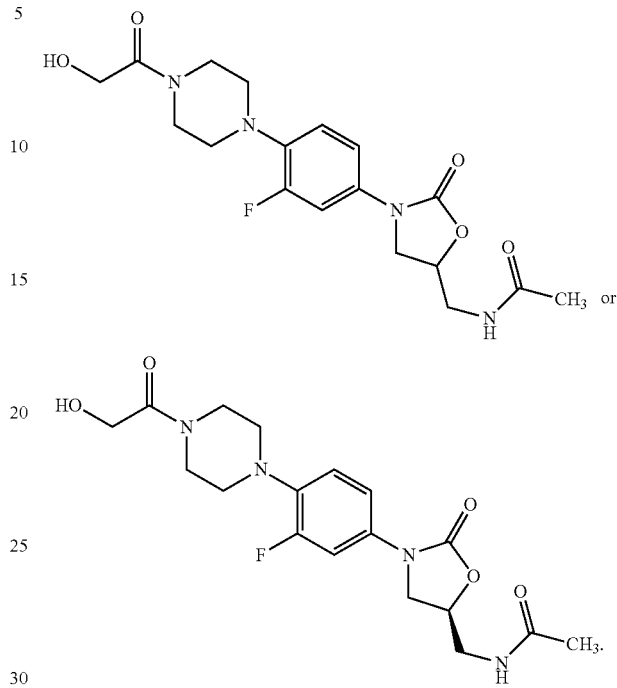

This embodiment includes (S)—N-[[3-[3-fluoro-4-[4-(hydroxyacetyl)-1-piperazinyl]phenyl-2-oxo-5-oxazolidinyl]methyl]acetamide, also known as eperezolid.

In another embodiment, the oxazolidinone antibiotic is a compound of the formula

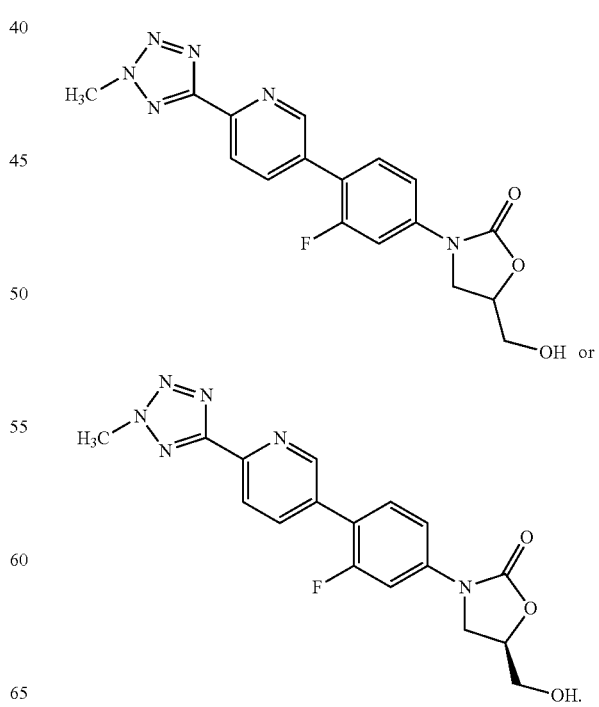

This embodiment includes (5R)-3-{3-fluoro-4-[6-(2-methyl-2H-tetrazol-5-yl)pyridin-3-yl]phenyl}-5-(hydroxymethyl)-1,3-oxazolidin-2-one, also known as torezolid.

In another embodiment, the oxazolidinone antibiotic is a compound of the formula

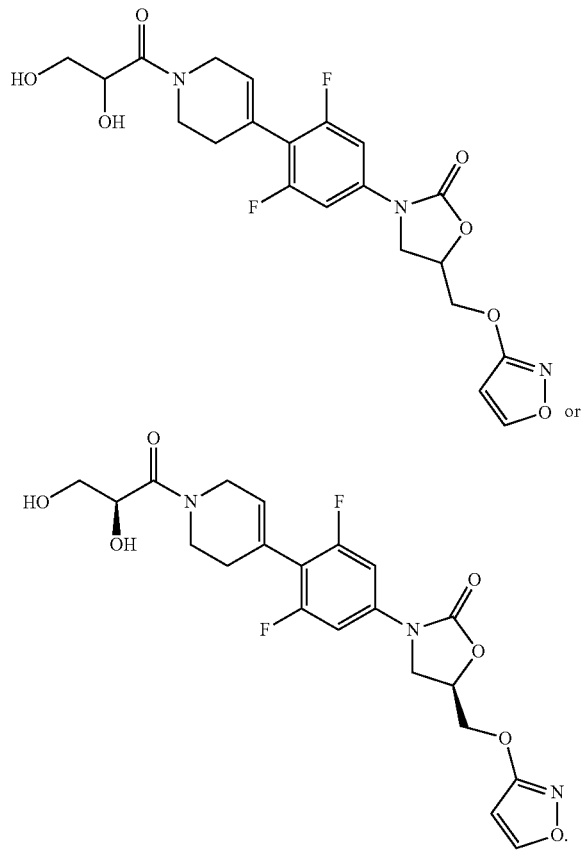

This embodiment includes (5R)-3-[4-[1-[(2S)-2,3-dihydroxypropanoyl]-3,6-dihydro-2H-pyridin-4-yl]-3,5-difluorophenyl]-5-(1,2-oxazol-3-yloxymethyl)-1,3-oxazolidin-2-one, also known as posizolid.

Additional illustrative oxazolidinone compounds useful in the methods, uses, compositions, and/or unit doses described herein, are known as antibiotic agents, for therapeutic and or prophylactic use against a number of human and veterinary pathogens, particularly against gram positive bacteria. Such compounds, including each of the formulae described herein, are referred to herein as "oxazolidinone antibiotics." Many of the oxazolidinone antibiotics are oxazolidin-2-ones characterized by a substituted aryl residue, such as a substituted phenyl group, or a substituted heteroaryl residue, such as a substituted pyridyl group, at the 3-position and a substituted lower alkyl residue, such as an aminoalkyl group, for example an aminomethyl group, in which the amino group bears an acyl or thioacyl residue, such as an acetyl group, at the 5-position. Additional illustrative oxazolidinone compounds are described in U.S. Pat. Nos. 4,948,801; 5,043,443; 5,130,306; 5,164,510; 5,231,188; 5,254,577; 5,547,950; 5,565,571; 5,568,792; 5,529,998; 5,627,181; 5,652,238; 5,684,023; 5,688,792; 5,698,574; 5,700,799; 5,735,545; 5,792,765; 5,827,857; 5,837,870; 5,843,967; 5,861,413; 5,869,659; 5,880,118; 5,898,574; 5,968,962; 5,977,373; 5,981,528; 6,069,145; 6,110,936; 6,194,441; 6,255,304; 6,441,005; 6,537,986; 6,617,339; and 6,743,811, the disclosures of which are incorporated herein by reference.

In another embodiment, there is provided a pharmaceutical composition comprising an oxazolidinone antibiotic as described in any of the above descriptions for the use of treating cancers, including malignant glioma, thyroid cancer, and melanoma, including borderline forms of malignant glioma, thyroid cancer, and melanoma.

In another embodiment, each of the methods, uses, compositions, and/or unit doses described herein also includes the step of administering a therapeutically effective amount of one or more amidoalkylbenzenes to a patient suffering from, or in need of relief from one or more forms of cancer. Illustrative amidoalkylbenzenes include, but are not limited to, agomelatine, ramelteon, tasimelteon, analogs and derivatives of any of the foregoing, and metabolites of any of the foregoing, and pharmaceutically acceptable salts of any of the foregoing. Additional amidoalkylbenzenes that may be included in the methods described herein are described in co-pending U.S. provisional patent application, titled "Amidoalkylbenzenes for Cancer Treatment", the disclosure of which is incorporated herein by reference in its entirety.

For any of the methods, uses, compositions, and/or unit doses described herein, one embodiment is one wherein the oxazolidinone antibiotic is administered in combination with an anti-cancer agent.

In a further embodiment, there is provided a pharmaceutical composition comprising an oxazolidinone antibiotic as described in any of the above descriptions together with a pharmaceutically acceptable carrier and an additional anti-cancer agent.

As used herein, an anti-cancer agent comprises an agent which is useful in the treatment of a specific type of cancer, such as malignant glioma, thyroid cancer or melanoma, or borderline forms of malignant glioma, thyroid cancer or melanoma, to be treated. Illustratively, the anti-cancer agent may be one of a number of cytotoxic or cytostatic chemothereapeutic agents, or may be a drug or antibody which is targeted to a specific mechanism relevant to the cancer, such as an inhibitor of a specific enzyme or an antagonist of a certain receptor relevant to the particular cancerous tissue. Such a drug or antibody may modulate tumor cell behavior without directly attacking the cell. The anti-cancer agent may be pharmacologically active itself or may serve as a prodrug for the pharmacologically active species.

Thus, for a method, use, composition, or unit dose described herein, one embodiment is one wherein the anti-cancer agent is selected from the group consisting of temozolomide, a corticosteroid, dacarbazine, carmustine, lomustine, vinblastine, vincristine, procarbazine, etoposide, irinotecan, bevacizumab, cetuximab, imatinib, gefitinib, erlotinib, tamoxifen, isotretinoin, thalidomide, vorinostat, bortezomib, interferon alpha-2b and a platinum-containing drug, such as one selected from cisplatin, carboplatin and oxaliplatin, and the like.

For any above method, use, composition, or unit dose, in one embodiment the treatment is for malignant glioma, or a borderline form of malignant glioma. In one embodiment, the glioma or borderline form thereof is an astrocytoma, an oligodendroglioma, an oligoastrocytoma, or an ependymoma, or borderline form thereof. In one embodiment, the glioma or borderline form thereof is an astrocytoma. In one embodiment, the glioma or borderline form thereof is an oligodendroglioma, or borderline form thereof. In one embodiment, the glioma or borderline form thereof is an oligoastrocytoma, or borderline form thereof. In one embodiment, the glioma or borderline form thereof is an ependymoma, or borderline form thereof.

For any above method, use, composition, or unit dose, wherein the treatment is for malignant glioma, or a borderline form of malignant glioma, in one embodiment the oxazolidinone antibiotic is administered in combination with a therapeutically effective amount of an additional anti-cancer agent or in combination with a therapeutically effective amount of radiotherapy. In one embodiment of the above method, use, composition, or unit dose, the oxazolidinone antibiotic is administered in combination with a therapeutically effective amount of one or more of agomelatine, temozolomide, a corticosteroid, carmustine, lomustine, vincristine, vinblastine, procarbazine, etoposide, irinotecan, bevacizumab, cetuximab, imatinib, gefitinib, erlotinib, tamoxifen, isotretinoin, thalidomide, vorinostat, bortezomib or a platinum-containing drug, such as one selected from cisplatin, carboplatin and oxaliplatin. In one embodiment, the anti-cancer agent is agomelatine. In one embodiment, the anti-cancer agent is temozolomide. In one embodiment, the anti-cancer agent is a corticosteroid. In one embodiment, the anti-cancer agent is carmustine. In one embodiment, the anti-cancer agent is lomustine. In one embodiment, the anti-cancer agent is vincristine and/or vinblastine. In one embodiment, the anti-cancer agent is procarbazine. In one embodiment, the anti-cancer agent is a platinum-containing drug, such as one selected from cisplatin, carboplatin and oxaliplatin. In one embodiment, the anti-cancer agent is etoposide. In one embodiment, the anti-cancer agent is irinotecan. In one embodiment, the anti-cancer agent is bevacizumab. In one embodiment, the anti-cancer agent is cetuximab. In one embodiment, the anti-cancer agent is imatinib. In one embodiment, the anti-cancer agent is imatinib. In one embodiment, the anti-cancer agent is gefitinib. In one embodiment, the anti-cancer agent is erlotinib. In one embodiment, the anti-cancer agent is tamoxifen. In one embodiment, the anti-cancer agent is isotretinoin. In one embodiment, the anti-cancer agent is thalidomide. In one embodiment, the anti-cancer agent is vorinostat. In one embodiment, the anti-cancer agent is bortezomib. In another embodiment, the oxazolidinone antibiotic is administered in combination with a therapeutically effective amount of radiotherapy.

It is understood that oxazolidinone antibiotics, such as linezolid, and the like, cross the blood-brain-barrier, and are therefore useful in treating malignant glioma, and borderline forms of malignant glioma.

For any above method, use, composition, or unit dose, in one embodiment the treatment is for melanoma, or borderline forms of melanoma. In one embodiment, the melanoma, or borderline form thereof, is superficial spreading melanoma, nodular melanoma, lentigo malignant melanoma or acral lentiginous melanoma. In one embodiment, the melanoma, or borderline form thereof, is superficial spreading melanoma. In one embodiment, the melanoma, or borderline form thereof, is nodular melanoma. In one embodiment, the melanoma, or borderline form thereof, is lentigo malignant melanoma. In one embodiment, the melanoma, or borderline form thereof, acral lentiginous melanoma.

For any above method, use, composition, or unit dose, wherein the treatment is for melanoma, or a borderline form of melanoma, in one embodiment the oxazolidinone antibiotic is administered in combination with a therapeutically effective amount of an anti-cancer agent or in combination with a therapeutically effective amount of radiotherapy. In one embodiment of the above method or use, the anti-cancer agent is agomelatine, dacarbazine, carmustine, vinblastine, tamoxifen, temozolomide, interferon alpha-2b or a platinum-containing drug, such as one selected from cisplatin, carboplatin and oxaliplatin. In one embodiment, the anti-cancer agent is agomelatine. In one embodiment, the anti-cancer agent is dacarbazine. In one embodiment, the anti-cancer agent is carmustine. In one embodiment, the anti-cancer agent is a platinum-containing drug, such as one selected from cisplatin, carboplatin and oxaliplatin. In one embodiment, the anti-cancer agent is vinblastine. In one embodiment, the anti-cancer agent is tamoxifen. In one embodiment, the anti-cancer agent is temozolomide. In one embodiment, the anti-cancer agent is interferon alpha-2b. In another embodiment, the oxazolidinone antibiotic is administered in combination with a therapeutically effective amount of radiotherapy.

For any above method, use, composition, or unit dose, in one embodiment the treatment is for thyroid cancer, or borderline forms of thyroid cancer. In one embodiment, the thyroid cancer, or borderline form thereof, is papillary, follicular, hurthle cell, medullary or anaplastic. In one embodiment, the thyroid cancer, or borderline form thereof, is papillary. In one embodiment, the thyroid cancer, or borderline form thereof, is follicular. In one embodiment, the thyroid cancer, or borderline form thereof, is hurthle cell. In one embodiment, the thyroid cancer, or borderline form thereof, is medullary. In one embodiment, the thyroid cancer, or borderline form thereof, is anaplastic.

For any above method, use, composition, or unit dose, wherein the treatment is for thyroid cancer, or a borderline form of thyroid cancer, in one embodiment the oxazolidinone antibiotic is administered in combination with a therapeutically effective amount of an anti-cancer agent or in combination with a therapeutically effective amount of radiotherapy, delivered either through external beam radiation and/or radioactive iodine. In one embodiment of the above method or use, the anti-cancer agent is agomelatine, levothyroxine, doxorubicin, bleomycin, vincristine, 5-fluorouracil, paclitaxel or a platinum-containing drug, such as one selected from cisplatin, carboplatin and oxaliplatin. In one embodiment, the anti-cancer agent is agomelatine. In one embodiment, the anti-cancer agent is levothyroxine. In one embodiment, the anti-cancer agent is doxorubicin. In one embodiment, the anti-cancer agent is bleomycin. In one embodiment, the anti-cancer agent is vincristine. In one embodiment, the anti-cancer agent is 5-fluorouracil. In one embodiment, the anti-cancer agent is a platinum-containing drug, such as one selected from cisplatin, carboplatin and oxaliplatin. In one embodiment, the anti-cancer agent is paclitaxel. In another embodiment, the oxazolidinone antibiotic is administered in combination with a therapeutically effective amount of radiotherapy, delivered through external beam radiation and/or radioactive iodine.

For any of the methods, uses, compositions, or unit doses that include co-therapy with one or more of the anticancer agents and/or radiotherapy, it is to be understood that the one or more oxazolidinone antibiotics are administered in combination with the one or more of the anticancer agents and/or radiotherapy.

The synthetic preparation of oxazolidinone antibiotics in well documented, for example in the patents listed above. Moreover, there is extensive documentation of preparation of various pharmaceutical compositions of oxazolidinone antibiotics for a number of modes of administration, including oral administration in solid and liquid forms, topical administration, and parenteral administration. A pharmaceutical composition comprising an oxazolidinone antibiotic and an anti-cancer agent may be prepared by a conventional method using methods known to those of skill in the art.

The oxazolidinone antibiotics have a chiral center at the C-5 position of the oxazolidinone ring. The invention described herein is understood to include the use of a mixture of the isomers, such as the racemic mixture, or the use of the isomer illustrated in formula (I) or formula (II) in substantially optically pure form. Some compounds of formula (I) or formula (II) may have other chiral centers. It is to be understood that the invention encompasses all such optical and diasteroisomers, and racemic mixtures, that produce activity against cancer, including malignant gliomas, thyroid cancer and melanoma, which can be evaluated using standard tests, such as those described herein.

As used herein, "halo" includes fluoro, chloro and bromo.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, $C_1$-$C_4$, and $C_1$-$C_3$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, "($C_1$-$C_8$)hydrocarbyl" means a univalent group formed by removing a hydrogen from a hydrocarbon and includes normal, branched, cyclic, bicyclic, bridged bicyclic and aromatic residues.

As used herein, "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like. As used herein, the term "5-membered-heteroaryl" includes C-linked 5-membered aromatic heterocyclic groups, each of which may be optionally substituted. Illustrative 5-membered-heteroaryl groups include, but are not limited to, thienyl, pyrazolyl, imidazolyl, oxazolyl, thiazolyl, isoxazolyl, isothiazolyl, oxadiazolyl, thiadiazolyl, and triazolyl groups.

The term "optionally substituted" as used herein includes the replacement of hydrogen atoms with other groups on the radical that is optionally substituted. Such other groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other groups on the aryl or heteroaryl that is optionally substituted. Such other groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein the term "malignant glioma" includes neuroectodermal tumors of neuroglial origin. It includes astrocytoma, oligodendroglioma, oligoastrocytoma and ependymoma derived from astrocytes, oligodendrocytes and ependymal cells. Many gliomas infiltrate brain tissue diffusely and irregularly. Astrocytomas are the most common gliomas. They are classified, in ascending order of malignancy, as Grade 1 or 2: Low-grade astrocytomas Grade 3: Anaplastic astrocytomas Grade 4: Glioblastomas, including glioblastoma multiforme, the most malignant (Shapiro et al 2008).

Glioblastoma multiforme are Grade IV astrocytomas composed of a heterogeneous mixture of poorly differentiated neoplastic astrocytes. Glioblastoma multiforme primarily affect adults, and are located preferentially in the cerebral hemispheres. Much less commonly, GBMs can affect the brain stem in children and the spinal cord. These tumors may develop from lower-grade astrocytomas (World Health Organization Grade II) or anaplastic astrocytomas (WHO Grade III), but, more frequently, they manifest de novo, without any evidence of a less malignant precursor lesion. Current treatment of glioblastomas is limited to palliative and includes surgery, radiotherapy, and chemotherapy.

As used herein the term "melanoma" includes malignant tumors of melanocytes which are found predominantly in skin but also in the GI tract and the eye (uveal melanoma). Melanoma accounts for only 4% of all skin cancers; however, it causes the greatest number of skin cancer-related deaths worldwide. Early detection of thin cutaneous melanoma is reportedly the best means of reducing mortality.

The sequence of events in which normal melanocytes transform into melanoma cells, referred to as melanoma genesis, is poorly understood. It likely involves a multistep process of progressive genetic mutations that (Demierre et al 2003) alter cell proliferation, differentiation, and death and (Whiteman et al, 2003) impact susceptibility to the carcinogenic effects of ultraviolet radiation. Recent data suggest multiple pathways of melanoma pathogenesis, with melanomas in sun-protected skin (trunk) developing in association with a high nevus count and intermittent ultraviolet radiation as opposed to those developing on sun-exposed skin in patients with low nevus counts and chronic sun exposure (Whiteman et al, 2003, Maldonado et al 2003). Primary cutaneous melanoma may develop in precursor melanocytic nevi (ie, common, congenital, and atypical/dysplastic types), although more than 60% of cases are believed to arise de novo, and not from a preexisting pigmented lesion.

The development of melanoma is multifactorial and appears to be related to multiple risk factors, including fair complexion, excessive childhood sun exposure and blistering childhood sunburns, an increased number of common and dysplastic moles, a family history of melanoma, the presence of a changing mole or evolving lesion on the skin, and, importantly, older age (Sober et al, 1979, Rhodes et al 1987, Williams et al, 1994).

The incidence of melanoma has more than tripled in the Caucasian population during the last 20 years, and melanoma currently is the sixth most common cancer in the United States. Approximately 68,720 Americans (39,080 men and 29,640 women) will develop invasive cutaneous melanoma in 2009, with an estimated additional 53,120 or more cases of melanoma in situ (Jemal et al, 2009). The incidence may be higher due to melanoma underreporting to cancer registries, particularly for tumors that are diagnosed and managed in the outpatient setting (Cockburn et al, 2008). The current lifetime risk for developing invasive melanoma is 1 case per 60 Americans, a 2000% increase since 1930. This risk rises to 1 case per 32 Americans if noninvasive melanoma in situ is included. While melanoma accounts for roughly 4% of all skin cancers, it is responsible for more than 74% of skin cancer deaths. In the United States, one person each hour dies from metastatic melanoma.

As used herein the term "thyroid cancer" includes any of five kinds of malignant tumors of the thyroid gland: papillary, follicular, medullary, hurthle cell, or anaplastic (Wartfsky et al, 2010). There are over 11,000 new cases of thyroid cancer each year in the US. Females are more likely to have thyroid cancer than men by a ratio of 3:1, and it is more common in people who have been treated with radiation to the head, neck, or chest. Thyroid cancer can occur in any age group, although it is most common after age 30 and its aggressiveness increases significantly in older patients. Rather than causing the whole thyroid gland to enlarge, a cancer usually causes small growths (nodules) within the thyroid. Although as many as 10% of the population will have thyroid nodules, the vast majority are benign. Only approximately 5% of all thyroid nodules are malignant. Nodules are more likely to be cancerous if only one nodule is found rather than several, if a thyroid scan shows that the nodule isn't functioning, if the nodule is solid rather than filled with fluid (cystic), if the nodule is hard, or if the nodule is growing quickly. Thus a nodule that is cold on scan is more likely to be malignant, but the majority of these are benign as well. Thyroid cancers often have a limited ability to take up iodine and produce thyroid hormone, but very rarely they produce enough hormone to cause hyperthyroidism. Symptoms that occur occasionally include hoarseness, neck pain, and enlarged lymph nodes, but it should be noted that the majority of patients present with a nodule on their thyroid that typically does not cause symptoms.

Papillary cancer accounts for up to 75% of all thyroid cancers. Two to three times as many women as men have papillary cancer; however, since nodules are far more common in women, a nodule in a man is more suspicious for a cancer. Papillary cancer is more common in young people (peak onset is 30-50 years of age) but grows and spreads more quickly in the elderly. Papillary carcinoma typically arises as an irregular, solid or cystic mass that arises from otherwise normal thyroid tissue. Prognosis is directly related to tumor size and a "good prognosis is associated with tumors less than 1.5 cm (½ inch) in size. This cancer has a high cure rate with ten year survival rates for all patients with papillary thyroid cancer estimated at 80-90%. Cervical metastasis (spread to lymph nodes in the neck) may also be present in 50% of small tumors and in over 75% of the larger thyroid cancers. The presence of lymph node metastasis in these cervical areas causes a higher recurrence rate but not a higher mortality rate. Distant metastasis (spread) is uncommon, but when it does occur the lung and bone are the most common sites. Tumors that invade or extend beyond the thyroid capsule have a worsened prognosis because of a high local recurrence rate.

Follicular cancer accounts for about 15 percent of all thyroid cancers and is considered more malignant (aggressive) than papillary carcinoma. Vascular invasion is characteristic for follicular carcinoma and therefore distant metastasis is more common. Distant metastasis may occur in a small primary. Lung, bone, brain, liver, bladder, and skin are potential sites of distant spread. Lymph node involvement is far less common than in papillary carcinoma (8-13%). In contrast to papillary cancer, follicular cancer occurs only rarely after radiation therapy and occurs in a slightly older age group (peak onset at 40-60 years of age) than papillary and is also less common in children. Follicular cancer is also more common in women than in men (3:1), but as with papillary cancer, a nodule in a man is more likely to be cancerous. Mortality is related to the degree of vascular invasion. Treatment for follicular cancer requires surgically removing as much of the thyroid gland as possible and destroying any remaining thyroid tissue, including the metastases, with radioactive iodine. Age is a very important factor in terms of prognosis. Patients over 40 have a more aggressive disease and typically the tumor does not concentrate iodine as well as in younger patients. Prognosis also is directly related to tumor size with s good prognosis associated with tumors less than 1.0 cm (⅜ inch) in size. Overall cure rate is high (near 95% for small lesions in young patients), but decreases with advanced age.

Medullary tumors are the third most common of all thyroid cancers (about 5-8%). Unlike papillary and follicular thyroid cancers which arise from thyroid hormone producing cells, medullary cancer of the thyroid originates from the parafollicular cells (also called C cells) of the thyroid. These C cells make a different hormone called calcitonin which regulates physiologic functions different than those controlled by thyroid hormone. In medullary cancer, the thyroid gland produces excessive amounts of calcitonin as well as other hormones, and thus it can cause unusual symptoms. This cancer tends to spread (metastasize) through the lymphatic system to the lymph nodes and through the blood to the liver, lungs, and bones. Medullary cancer can develop along with other types of endocrine cancers in what is called multiple endocrine neoplasia (MEN) syndrome. Medullary cancer has a much lower cure rate than does the "well differentiated" thyroid cancers (papillary and follicular), but cure rates are higher than they are for anaplastic thyroid cancer. Overall 10 year survival rates are 90% when all the disease is confined to the thyroid gland, 70% with spread to cervical lymph nodes, and 20% when spread to distant sites is present.

Anaplastic tumors are the least common (about 2-3%) and most deadly of all thyroid cancers. These tumors occur most commonly in elderly women (peak onset older than 65), and extremely rare in young patients. This cancer grows very quickly and usually causes a large growth in the neck. The most common way this cancer becomes evident is by the patient or his/her family member noticing a growing neck mass. About 80 percent of the people with anaplastic cancer die within 1 year. Treatment with radioactive iodine is reportedly unsuccessful because anaplastic cancers do not concentrate radioactive iodine. However, treatment with anticancer drugs and radiation therapy before and after surgery has resulted in some cures.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

In addition, in those embodiments described herein drawn to combination therapy or co-therapy comprising administration of an oxazolidinone antibiotic and an anti-cancer agent, "therapeutically effective amount" refers to that amount of the combination of agents taken together so that the combined effect elicits the desired biological or medicinal response. For example, the therapeutically effective amount of For example, the therapeutically effective amount of linezolid and agomelatine, linezolid and temozolomide, and the like, would be the amount of linezolid and the amount agomelatine, or the amount of linezolid and the amount of the temozolomide, and the like that when taken together or sequentially have a combined effect that is therapeutically effective. Further, it is appreciated that in some embodiments of such methods that include co-administration, the amount of oxazolidinones, agomelatine, and/or temozolomide, and the like when taken individually may or may not be therapeutically effective. It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

In one embodiment, pharmaceutical compositions are described herein. Illustrative pharmaceutical compositions include dosage forms of one or more oxazolidinone antibiotics and/or pharmaceutically acceptable salts thereof, and one or more pharmaceutically acceptable carriers, excipients, and/or diluents therefor. Other illustrative pharmaceutical compositions include (a) mixtures of one or more oxazolidinone antibiotics and/or pharmaceutically acceptable salts thereof, and agomelatine and/or pharmaceutically acceptable salts thereof, (b) mixtures of one or more oxazolidinone antibiotics and/or pharmaceutically acceptable salts thereof, and one or more chemotherapeutic agents, including corticosteroids, carmustine, lomustine, vincristine, procarbazine, platin-containing drug (cisplatin, carboplatin or oxaliplatin), irinotecan, bevacizumab, cetuximab, imatinib, gefitinib, erlotinib, tamoxifen, isotretinoin, thalidomide, vorinostat, bortezomib, dacarbazine, interferon alpha-2b, doxorubycin, bleomycin, 5-fluoruracil, paclitaxel and/or pharmaceutically acceptable salts thereof, and (c) mixtures of one or more oxazolidinone antibiotics and/or pharmaceutically acceptable salts thereof, and levothyroxine and/or pharmaceutically acceptable salts thereof. Other illustrative formulations include "sandwich" formulations where two or more separate drug dosage forms are conveniently adhered one to the other for simultaneous co-administration.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustratively, administering includes local use, such as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

As described above, the compounds or compositions described herein may be administered orally in the form of tablets, capsules, elixirs or syrups, or rectally in the form of suppositories. Parenteral administration of a compound is suitably performed, for example, in the form of saline solutions or with the compound incorporated into liposomes. In cases where the compound in itself is not sufficiently soluble to be dissolved, a solubilizer such as ethanol can be applied.

In another embodiment, the oxazolidinone antibiotic, or a pharmaceutically acceptable salt thereof, is administered to a patient in need of relief at a daily dose in the range from about 1 mg to about 3,000 mg per day; from about 100 mg to about 1200 mg per day, from about 200 mg to about 900 mg per day, from about 400 mg to about 1200 mg per day, from about 800 mg to about 1200 mg per day, from about 600 mg to about 1000 mg per day. The foregoing doses may be administered to adults and/or teens, and the corresponding doses administered to preteens, toddlers, or infants, are lower, such as illustratively by a factor of about 2, about 5, or about 10, respectively. Each of the foregoing may be illustratively administered q.d., b.i.d., t.i.d, or by other conventional dosing protocols, including intermittent dosing protocols that have an off period. In addition, it is to be understood that at each dosing interval, the amount of the dose may be single or divided into various unit dosage forms. In another illustrative embodiment, the daily dose is administered t.i.d.

Without limiting the foregoing, it is appreciated that lower doses of oxazolidinone antibiotics may be more applicable to an ongoing, or chronic therapy, designed for continuous administration, rather than intermittent or acute administration. Accordingly, the daily dose may be divided and administered b.i.d. and/or t.i.d, although it is to be understood that q.d. dosing is described herein. It is to be understood that the illustrative doses described herein represent daily doses, and may be therefore administered q.d., b.i.d., t.i.d., and according to additional dosing protocols. In addition, it is to be understood that the doses may be single or divided.

In another embodiment the methods described herein include a titration step where the dose is gradually increased over a predetermined time period, such as a two step or three step protocol. The foregoing tritrating dosing protocols may be administered to adults and/or teens, and the corresponding doses administered to preteens, toddlers, or infants, are lower, such as illustratively by a factor of about 2, about 5, or about 10, respectively, and may accordingly be based on the weight of the patient as indicated.

Optimal dosages and dosage regimens to be administered may be readily determined by routine experimentation, and it is understood that such optimal dosages and dosage regimens will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens.

In addition to the foregoing illustrative dosages and dosing protocols, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

In another illustrative embodiment, kits or packages are described herein. Illustrative kits and packages include preparations where the co-administered compounds are placed in a format following the dosing protocols described herein. For example, an illustrative package may include a grid pattern, wherein each section includes a dual or triple bubble pack for the one or more oxazolidinone antibiotic dosages, and illustratively the agomelatine dosage and the temozolomide dosage. For example, as one embodiment, there is provided a kit comprising a pharmaceutical composition of an oxazolidinone antibiotic, as described herein, and a pharmaceutical composition of an anti-cancer agent, as described herein. In one embodiment, the kit is a unit dose form, comprising one or more dosage units of an oxazolidinone antibiotic and one or more dosage units of an anti-cancer agent.

Additional illustrative embodiments of the invention are described by the following numbered clauses:

1. A method for treating malignant glioma, thyroid cancer or melanoma, or borderline forms of malignant glioma, thyroid cancer or melanoma, the method comprising the step of administering to a patient in need thereof a therapeutically effective amount of an oxazolidinone antibiotic, or a pharmaceutically acceptable salt thereof;

2. Use of an oxazolidinone antibiotic, or a pharmaceutically acceptable salt thereof, for treating malignant glioma, thyroid cancer or melanoma, or borderline forms of malignant glioma, thyroid cancer or melanoma;

3. Use of an oxazolidinone antibiotic, or a pharmaceutically acceptable salt thereof, for the manufacture of a medicament for treating malignant glioma, thyroid cancer or melanoma, or borderline forms of malignant glioma, thyroid cancer or melanoma;

4. The method or use of any of the previous clauses wherein the oxazolidinone antibiotic is a compound of formula (I)

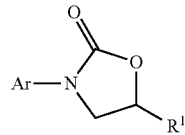

(I)

wherein Ar is an optionally substituted aryl or heteroaryl group and $R^1$ is an N-substituted amino(1-3C)alkyl group, a hydroxy(1-3C)alkyl group or a (5-membered-heteroaryl)oxy(1-3C)alkyl group;

5. The method or use of any of the previous clauses wherein Ar is a group

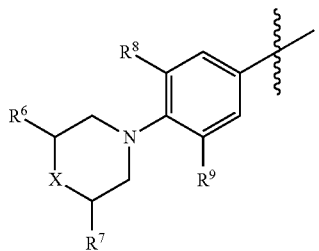

wherein X is O, S, SO, $SO_2$, $SNR^4$, $S(O)NR^4$, $NR^4$ or $NC(O)CH_2OR^4$, wherein $R^4$ is selected from hydrogen, $R^5$ and $C(O)R^5$ groups wherein $R^5$ is $(C_1$-$C_8)$ hydrocarbyl optionally substituted with one or more hydroxy, fluorine or chlorine groups; $R^6$ and $R^7$ are independently selected from hydrogen, methyl and cyano groups; and $R^8$ and $R^9$ are independently selected from hydrogen, fluorine and chlorine atoms; or alternatively, $R^6$ and $R^7$ are hydrogen, one of $R^8$ and $R^9$ is fluorine and the other of $R^8$ and $R^9$ is hydrogen;

6. The method or use of any of the previous clauses wherein $R^1$ is a group $(CH_2)_nN(R^2)COR^3$, a group $(CH_2)_nOH$ or a group $(CH_2)_nOR^{10}$ wherein n is 1, 2 or 3, and $R^2$ and $R^3$ are independently selected from hydrogen and $(C_1$-$C_8)$ hydrocarbyl optionally substituted with one or more hydroxy, fluorine or chlorine groups and $R^{10}$ is a C-linked 5-membered heteroaryl ring containing 2 to 4 heteroatoms independently selected from N, O and S, which ring is optionally substituted on an available carbon atom by 1 or 2 substituents independently selected from $(C_1$-$C_4)$ alkyl, amino, $(C_1$-$C_4)$ alkylamino, $(C_1$-$C_4)$ alkoxy and halo, and/or on an available nitrogen atom, provided the ring is not thereby quaternized, by $(C_1$-$C_4)$ alkyl;

7. The method or use of any of the previous clauses wherein the oxazolidinone antibiotic is (S)—N-[[3-[3-fluoro-4-(4-morpholinyl)phenyl-2-oxo-5-oxazolidinyl]methyl]acetamide, N-[(5S)-3-[[3-fluoro-4-[4-(2-fluoroethyl)-3-oxopiperazin-1-yl]phenyl]-2-oxooxazolidin-5-yl]methyl]acetamide, N-[[(5S)-3-[4-(1,1-dioxido-4-thiomorpholinyl)-3,5-difluorophenyl]-2-oxo-5-oxazolidinyl]methyl]acetamide, (S)—N-[[3-[5-(4-pyridyl)pyrid-2-yl]-2-oxo-5-oxazolidinyl]methyl]acetamide, or (S)—N-[[3-[5-(3-pyridyl)thiophen-2-yl]-2-oxo-5-oxazolidinyl]methyl]acetamide;

8. The method or use of any of the previous clauses wherein the oxazolidinone antibiotic is N-[[(5S)-3-[4-(1,1-dioxido-4-thiomorpholinyl)-3,5-difluorophenyl]-2-oxo-5-oxazolidinyl]methyl]acetamide;

9. The method or use of any of the previous clauses wherein the oxazolidinone antibiotic is a compound of the formula

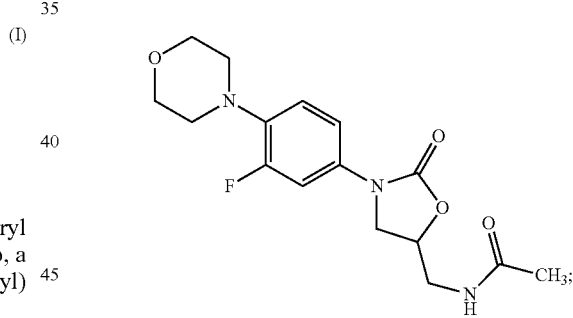

10. The method or use of any of the previous clauses wherein the oxazolidinone antibiotic is a compound of the formula

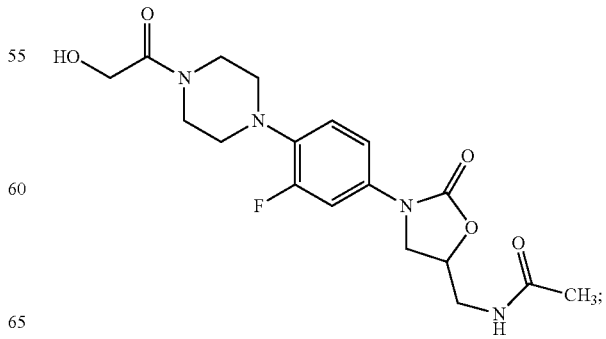

11. The method or use of any of the previous clauses wherein the oxazolidinone antibiotic is a compound of the formula

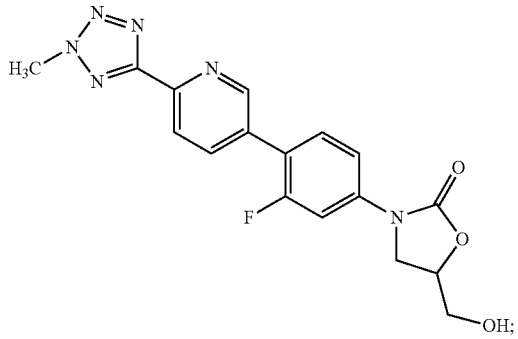 [SMILES: Cn1nnc(-c2ccc(-c3ccc(N4CC(CO)OC4=O)cc3F)cn2)n1]

12. The method or use of any of the previous clauses wherein the oxazolidinone antibiotic is a compound of the formula

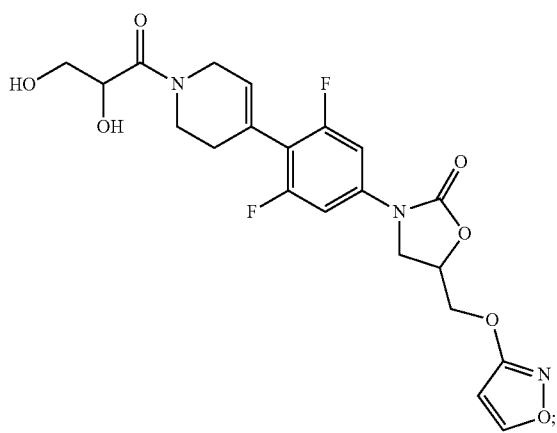 [SMILES: O=C(C(O)CO)N1CC=C(c2c(F)cc(N3CC(COc4ccon4)OC3=O)cc2F)CC1]

13. The method or use of any of the previous clauses wherein the oxazolidinone antibiotic is administered in combination with an anti-cancer agent;

14. A pharmaceutical composition comprising an oxazolidinone antibiotic as described in any of the previous clauses for the use of treating malignant glioma, thyroid cancer or melanoma;

15. The method, use or composition of any of the previous clauses wherein the anti-cancer agent is selected from the group consisting of agomelatine, temozolomide, a corticosteroid, dacarbazine, carmustine, lomustine, vinblastine, vincristine, procarbazine, etoposide, irinotecan, bevacizumab, cetuximab, imatinib, gefitinib, erlotinib, tamoxifen, isotretinoin, thalidomide, vorinostat, bortezomib, interferon alpha-2b and a platinum-containing drug, selected from cisplatin, carboplatin and oxaliplatin;

16. The method or use of any of the previous clauses wherein the treatment is for malignant glioma, or a borderline form of malignant glioma;

17. The method or use of any of the previous clauses wherein the glioma or borderline form thereof is an astrocytoma, an oligodendroglioma, an oligoastrocytoma, or an ependymoma, or borderline form thereof;

18. The method or use of any of the previous clauses wherein the glioma or borderline form thereof is an astrocytoma, or borderline form thereof;

19. The method or use of any of the previous clauses wherein the glioma or borderline form thereof is an oligodendroglioma, or borderline form thereof;

20. The method or use of any of the previous clauses wherein the glioma or borderline form thereof is an oligoastrocytoma, or borderline form thereof;

21. The method or use of any of the previous clauses wherein the glioma or borderline form thereof is an ependymoma, or borderline form thereof;

22. The method or use of any of the previous clauses wherein the oxazolidinone antibiotic is administered in combination with a therapeutically effective amount of an anti-cancer agent or in combination with a therapeutically effective amount of radiotherapy;

23. The method or use of any of the previous clauses wherein the anti-cancer agent is agomelatine, temozolomide, a corticosteroid, carmustine, lomustine, vincristine, procarbazine, etoposide, irinotecan, bevacizumab, cetuximab, imatinib, gefitinib, erlotinib, tamoxifen, isotretinoin, thalidomide, vorinostat, bortezomib or a platinum-containing drug selected from cisplatin, carboplatin and oxaliplatin;

24. The method or use of any of the previous clauses wherein the anti-cancer agent is agomelatine;

25. The method or use of any of the previous clauses wherein the anti-cancer agent is temozolomide;

26. The method or use of any of the previous clauses wherein the oxazolidinone antibiotic is administered in combination with a therapeutically effective amount of radiotherapy;

27. The method or use of any of the previous clauses wherein the treatment is for melanoma, or a borderline form of melanoma;

28. The method or use any of the previous clauses wherein the melanoma, or borderline form thereof, is superficial spreading melanoma, nodular melanoma, lentigo maligna melanoma or acral lentiginous melanoma;

29. The method or use any of the previous clauses wherein the melanoma, or borderline form thereof, is superficial spreading melanoma;

30. The method or use any of the previous clauses wherein the melanoma, or borderline form thereof, is nodular melanoma;

31. The method or use any of the previous clauses wherein the melanoma, or borderline form thereof, is lentigo maligna melanoma;

32. The method or use any of the previous clauses wherein the melanoma, or borderline form thereof, is acral lentiginous melanoma;

33. The method or use of any of the previous clauses wherein the oxazolidinone antibiotic is administered in combination with a therapeutically effective amount of an anti-cancer agent or in combination with a therapeutically effective amount of radiotherapy;

34. The method or use any of the previous clauses wherein the anti-cancer agent is agomelatine, dacarbazine, carmustine, vinblastine, tamoxifen, temozolomide, interferon alpha-2b or a platinum-containing drug selected from cisplatin, carboplatin and oxaliplatin;

35. The method or use any of the previous clauses wherein the anti-cancer agent is agomelatine;

36. The method or use any of the previous clauses wherein the anti-cancer agent is temozolomide;

37. The method or use any of the previous clauses wherein the oxazolidinone antibiotic is administered in combination with a therapeutically effective amount of radiotherapy;

38. The method or use of any of the previous clauses wherein the treatment is for thyroid cancer, or borderline forms of thyroid cancer;

39. The method or use any of the previous clauses wherein the thyroid cancer, or borderline form thereof, is papillary, follicular, hurthle cell, medullary or anaplastic;

40. The method or use any of the previous clauses wherein the thyroid cancer, or borderline form thereof, is papillary;

41. The method or use any of the previous clauses wherein the thyroid cancer, or borderline form thereof, is follicular;

42. The method or use any of the previous clauses wherein the thyroid cancer, or borderline form thereof, is hurthle cell;

43. The method or use any of the previous clauses wherein the thyroid cancer, or borderline form thereof, is medullary;

44. The method or use any of the previous clauses wherein the thyroid cancer, or borderline form thereof, is anaplastic;

45. The method or use of any of the previous clauses wherein the oxazolidinone antibiotic is administered in combination with a therapeutically effective amount of an anti-cancer agent or in combination with a therapeutically effective amount of radiotherapy, delivered either through external beam radiation and/or radioactive iodine;

46. The method or use any of the previous clauses wherein the anti-cancer agent is agomelatine, levothyroxine, doxorubicin, bleomycin, vincristine, 5-fluoruracil, paclitaxel or a platinum-containing drug selected from cisplatin, carboplatin and oxaliplatin;

47. The method or use of any of the previous clauses wherein the anti-cancer agent is agomelatine;

48. The method or use of any of the previous clauses wherein the oxazolidinone antibiotic is administered in combination with a therapeutically effective amount of radiotherapy, delivered through external beam radiation and/or radioactive iodine;

49. A kit comprising a pharmaceutical composition of an oxazolidinone antibiotic, as described in any of any of the previous clauses, and a pharmaceutical composition of an anti-cancer agent, as described in any of the previous clauses;

50. The kit of any of the previous clauses wherein the kit is a unit dose form, comprising one or more dosage units of an oxazolidinone antibiotic and one or more dosage units of an anti-cancer agent;

51. A pharmaceutical composition comprising an oxazolidinone antibiotic as described in any of the previous clauses together with a pharmaceutically acceptable carrier and an anti-cancer agent;

The effective use of the methods described herein for treating or ameliorating malignant glioma, melanoma and thyroid cancer using one or more compounds described herein may be based upon cell line and animal models, such as murine and rabbit models. For example, it is understood that malignant glioma, melanoma and thyroid cancer are characterized by uncontrolled cellular proliferation, which can be studied in culture of the corresponding malignant cell lines. Malignant glioma, melanoma and thyroid cancer are also characterized by the development of symptoms, each of which may be elicited in animals, such as mice and rabbits, and other surrogate test animals. Illustrative cell line models of malignant glioma, melanoma and thyroid cancer that may be used to evaluate the methods of treatment and the pharmaceutical compositions described herein to determine the therapeutically effective amounts described herein, include but not limited to the HT-144, A172 and SW-579 cell lines.

The following examples further illustrate specific embodiments of the invention; however, the following illustrative examples should not be interpreted in any way to are to limit invention.

EXAMPLES

Clinical Examples

EXAMPLE. Linezolid, torezolid, posizolid, eprezolid, or a combination thereof, (600 mg) is administered two times daily to a patient suffering from or in need of relief from malignant glioma, melanoma or thyroid cancer. Illustratively, the linezolid is in the dosage form of tablets (comprising 600 mg of linezolid, 30 mg of lactose, and 5 mg of magnesium stearate) for oral administration. The duration of treatment in this and other examples described herein is determined according to the progression of malignant glioma, melanoma or thyroid cancer in each individual patient and dose adjustments are made accordingly. Treatment efficacy in this and other examples described herein may be monitored by any conventional technique or method, including self-reporting, observations of an attending physician, diagnostic methods, and imaging methods, such as CT, MRI, and the like, and the results of treatment are evaluated statistically, illustratively by using Student's t-test and/or Fisher's "Fi" criterion, or other conventional statistical evaluation.

The following examples are carried out in a similar manner:

EXAMPLE. Linezolid, torezolid, posizolid, eprezolid, or a combination thereof, (50 mg) is administered two times daily to an adult or a child.

EXAMPLE. Linezolid, torezolid, posizolid, eprezolid, or a combination thereof, (100 mg) is administered two times daily to an adult or a child.

EXAMPLE. Linezolid, torezolid, posizolid, eprezolid, or a combination thereof, (150 mg) is administered two times daily to an adult or a child.

EXAMPLE. Linezolid, torezolid, posizolid, eprezolid, or a combination thereof, (200 mg) is administered two times daily to an adult or a child.

EXAMPLE. Linezolid, torezolid, posizolid, eprezolid, or a combination thereof, (250 mg) is administered two times daily to an adult or a child.

EXAMPLE. Linezolid, torezolid, posizolid, eprezolid, or a combination thereof, (300 mg) is administered two times daily to an adult or a child.

EXAMPLE. Linezolid, torezolid, posizolid, eprezolid, or a combination thereof, (350 mg) is administered two times daily to an adult or a child.

EXAMPLE. Linezolid, torezolid, posizolid, eprezolid, or a combination thereof, (400 mg) is administered two times daily to an adult or a child.

EXAMPLE. Linezolid, torezolid, posizolid, eprezolid, or a combination thereof, (450 mg) is administered two times daily to an adult or a child.

EXAMPLE. Linezolid, torezolid, posizolid, eprezolid, or a combination thereof, (500 mg) is administered two times daily to an adult or a child.

EXAMPLE. Linezolid, torezolid, posizolid, eprezolid, or a combination thereof, (550 mg) is administered two times daily to an adult or a child.

EXAMPLE. Linezolid, torezolid, posizolid, eprezolid, or a combination thereof, (700 mg) is administered two times daily to an adult or a child.

EXAMPLE. Linezolid, torezolid, posizolid, eprezolid, or a combination thereof, (800 mg) is administered two times daily to an adult or a child.

EXAMPLE. Linezolid, torezolid, posizolid, eprezolid, or a combination thereof, (900 mg) is administered two times daily to an adult or a child.

EXAMPLE. Linezolid, torezolid, posizolid, eprezolid, or a combination thereof, (1000 mg) is administered two times daily to an adult or a child.

EXAMPLE. Linezolid, torezolid, posizolid, eprezolid, or a combination thereof, is administered as described herein, such as oral administration of 600 mg, two times daily, and co-administered with oral temozolomide (100 mg tablet, Schering-Plough Inc) once daily.

EXAMPLE. Linezolid, torezolid, posizolid, eprezolid, or a combination thereof, is administered as described herein, such as oral administration of 600 mg, two times daily, and co-administered with i.v. dacarbazine (DTIC-Dome, Bayer Healthcare), 4.5 mg/kg/day, for 10 days.

EXAMPLE. Linezolid, torezolid, posizolid, eprezolid, or a combination thereof, is administered as described herein, such as oral administration of 600 mg, two times daily, and co-administered with i.v. dacarbazine (DTIC-Dome, Bayer Healthcare), 4.5 mg/kg/day, for 10 days.

EXAMPLE. Linezolid, torezolid, posizolid, eprezolid, or a combination thereof, is administered as described herein, such as oral administration of 200 mg, two times daily, to a patient diagnosed with melanoma, and co-administered with iv dacarbazine (DTIC-Dome, Bayer Healthcare), 4.5 mg/kg/day for 10 days, and co-administered with oral temozolomide (100 mg tablet, Schering-Plough Inc) once daily for 28 days.

EXAMPLE. Linezolid, torezolid, posizolid, eprezolid, or a combination thereof, is administered as described herein, such as oral administration of 600 mg, two times daily, to a patient diagnosed with glioblastoma multiforme, and co-administered with oral temozolomide (100 mg tablet, Schering-Plough Inc) once daily for 28 days.

EXAMPLE. Linezolid, torezolid, posizolid, eprezolid, or a combination thereof, is administered as described herein, such as oral administration of 600 mg, two times daily, to a patient diagnosed with thyroid cancer, and co-administered with 60 mg/m$^2$ doxorubicin (50 mg/25 mL vial, Centocor Ortho Biotech Inc) as one single injection every 21-28 days, for four cycles.

In Vitro Examples

EXAMPLE. Oxazolidinone antibiotics and/or pharmaceutically acceptable salts thereof, including the compounds described herein, are efficacious in the A375, C32, SK-MEL-2, HT-144, A172, SNB-19, U87-MG and SW-579 cell line model, where the drugs being investigated are assayed for maximum inhibition over a range of 50 nM to 1 mM, in triplicate, in standard 96-well plates.

EXAMPLE. Cancer cell lines assay. Compounds are assayed for $IC_{50}$ over a range of 50 nM to 1 mM, in triplicate, in standard 96-well plates. Initially, the number of cells in each line to plate on day 0 is determined, in order to have <80% confluency on day 5. Cells are plated on day 0. Cells are allowed to adhere 4 hours prior to adding the compound. On day 5 Alamar Blue is added to the media of the cells at 10% of the total volume of the well and incubated for approximately 4 hours at tissue culture conditions. The Alamar Blue reagent consists of an oxidation-reduction indicator that yields a colorimetric change and a fluorescent signal in response to metabolic activity. The dose response curves is evaluated in a BioTek Synergy 2 plate reader. The readout fluorescence values are then be exported to spreedsheet software, such as Microsoft Excel or GraphPad, and are graphed to show the reduction in relative cell number in response to compounds added to culture. Maximum inhibition is expressed as the maximum of:

$$\frac{\left[\begin{array}{c}\text{(number of cells in the untreated well)} - \\ \text{(number of cells in the treated well)}\end{array}\right]}{\text{(number of cells in the untreated well)}}$$

over all dosages tested for each drug.

EXAMPLE. Linezolid is diluted in DMSO. One vial is thawed and administered on day 0, at concentrations 10 µM to 1 mM. Paclitaxel (0.1 µM) is used as a positive control. DMSO alone is used as a negative control. On day 5 Alamar Blue is added to the media of the cells at 10% of the total volume of the well and incubated for approximately 4 hours at tissue culture conditions.

TABLE

| Cell Line | Linezolid $IC_{50}$ | Linezolid Concentration | Linezolid % Maximum inhibition relative to negative control Statistical significance of Linezolid vs Non-treated (p, Student's t-test) | Paclitaxel % Maximum inhibition relative to negative control |
|---|---|---|---|---|
| HT-144 (Melanoma) | 500 µM | 1 mM | 90.7 (0.00250) | 86.9 |
| A172 (Malignant glioma) | 600-700 µM | 1 mM | 81.8 (6 × 10$^{-6}$) | 92.9 |
| C32 (Melanoma) | N/A | 1 mM | 26.1 (0.000720) | 90.8 |
| SW-579 (Thyroid Cancer) | N/A | 412 µM | 14.5 (0.0490) | N/A |

The following publications, and each additional publication cited herein are incorporated herein by reference.

Armstrong J S. The role of the mitochondrial permeability transition in cell death. Mitochondrion. 2006; 6:225-234.

Barker D, Wright E, Nguyen K, Cannon L, Fain P, Goldgar D, Bishop D T, Carey J, Baty B, Kivlin J, et al. Gene for von Recklinghausen neurofibromatosis is in the pericentromeric region of chromosome 17. Science. 1987 May 29; 236(4805).-1100-2.

Barth A, Wanek L A, Morton D L. Prognostic factors in 1,521 melanoma patients with distant metastases. J Am Coll Surg. 1995 September; 181(3):193-201.

Bovet P, Lob M. [Cancer mortality among the workers of a Swiss rubber goods factory. Epidemiological study, 1955-75] [Article in French]. Schweiz Med. Wochenschr. 1980 Aug. 30; 110(35):1277-87.

Capizzi P J, Donohue J H. Metastatic melanoma of the gastrointestinal tract: a review of the literature. Compr Ther. 1994; 20(1):20-3.

Carew J S, Huang P. Mitochondrial defects in cancer. Mol. Cancer. 2002 Dec. 9; 1:9.

Chudnovsky Y, Khavari P A, Adams A E. Melanoma genetics and the development of rational therapeutics. J Clin Invest. 2005 April; 115(4):813-24.

Cockburn M, Swetter S M, Peng D, Keegan T H, Deapen D, Clarke C A. Melanoma underreporting: why does it happen, how big is the problem, and how do we fix it?. J Am Acad Dermatol. December 2008; 59(6):1081-5.

Copeland D D, Bigner D D. Glial-mesenchymal tropism of in vivo avian sarcoma virus neuro-oncogenesis in rats. Acta Neuropathol. 1978 Jan. 19; 41 (1): 23-5.

Costantini P, Belzacq A S, Vieira H L, Larochette N, De Pablo M A, Zamzami N, et al. Oxidation of a critical thiol residue of the adenine nucleotide translocator enforces Bcl-2-independent permeability transition pore opening and apoptosis. Oncogene. 2000; 19:307-314.

Cutler S. J. Young J. L. eds. Third National Cancer Survey: Incidence Data. National Cancer Institute Monograph 41, Department of Health, Education and Welfare Publ. No. 75-787: National Cancer Institute Bethesda, Md. 1975.

Demierre M F, Nathanson L. Chemoprevention of melanoma: an unexplored strategy. J Clin Oncol. Jan. 1, 2003; 21(1):158-65.

Dinapoli R P, Brown L D, Arusell R M, Earle J D, O'Fallon J R, Buckner J C, Scheithauer B W, Krook J E, Tschetter L K, Maier J A, et al. North Central Cancer Treatment Group, Rochester, Minn. Phase III comparative evaluation of PCNU and carmustine combined with radiation. therapy for high-grade glioma. J Clin Oncol. 1993 Jul; 11 (7): 1316-21.

Frankel S A, German W J. Glioblastoma multiforme; review of 219 cases with regard to natural history, pathology, diagnostic methods, and treatment. J. Neurosurg. 1958 September; 15(5):489-503.

Jemal A, Siegel R, Ward E, Hao Y, Xu J, Thun M J. Cancer statistics, 2009. CA Cancer J. Clin. July-August 2009; 59(4):225-49.

Lena A, Rechichi M, Salvetti A, Bartoli B, Vecchio D, Scarcelli V, Amoroso R, Benvenuti L, Gagliardi R, Gremigni V, Rossi L. Drugs targeting the mitochondrial pore act as cytotoxic and cytostatic agents in temozolomide-resistant glioma cells. J Transl Med. 2009 Feb. 5; 7:13.

Maldonado J L, Fridlyand J, Patel H, et al. Determinants of BRAF mutations in primary melanomas. J Natl Cancer Inst. Dec. 17 2003; 95(24):1878-90.

Maximo V, Lima J, Soares P, Sobrinho-SimOes M. Mitochondria and cancer. Virchows Arch. 2009 May; 454(5): 481-95.

McKee E E, Ferguson M, Bentley A T, Mark A T. Inhibition of Mammalian Mitochondrial Protein Synthesis by Oxazolidinones. Antimicrob Agents Chemother. 2006 June; 50(6):2042-9.

McLaughlin J K, Malker H S, Blot W J, Malker B K, Stone B J, Weiner J A, Ericsson J L, Fraumeni J F Jr. Occupational risks for intracranial gliomas in Sweden. J Natl Cancer Inst. 1987 February; 78(2):253-7.

Moss A R. Occupational exposure and brain tumors. J Toxicol Environ Health. 1985; 16 (5): 703-11.

Rhodes A R, Weinstock M A, Fitzpatrick T B, Mihm M C Jr, Sober A J. Risk factors for cutaneous melanoma. A practical method of recognizing predisposed individuals. JAMA. Dec. 4, 1987; 258(21):3146-54.

Rudolf K, Cervinka M, Rudolf E. Cytotoxicity and mitochondrial apoptosis induced by etoposide in melanoma cells. Cancer Invest. 2009 August; 27(7):704-17.

Shapiro W. Gliomas. The Merck Manuals Online Medical Library. Revision February, 2008. http://www.merck.com/mmpe/sec16/ch225/ch225b.html?qt=ch225b&alt=sh Shapiro W R. Therapy of adult malignant brain tumors: what have the clinical trials taught us? Semin Oncol. 1986 March; 13(1):38-45.

Smith K R Jr, Wilson C B, Strike T A. Randomized comparisons of radiotherapy and nitrosoureas for the treatment of malignant glioma after surgery. N Engl J. Med. 1980 Dec. 4; 303 (23): 1323-9.

Sober A J, Fitzpatrick T B, Mihm M C, et al. Early recognition of cutaneous melanoma. JAMA. Dec. 21, 1979; 242(25):2795-9.

Walker M D, Alexander E Jr, Hunt W E, MacCarty C S, Mahaley M S Jr, Mealey J Jr, Norrell H A, Owens G, Ransohoff J; Wilson C B, Gehan E A, Strike T A. Evaluation of BCNU and/or radiotherapy in the treatment of anaplastic gliomas. A cooperative clinical trial. J. Neurosurg. 1978 September; 49(3):333-43.

Walker M D, Green S B, Byar D P, Alexander E Jr, Batzdorf U, Brooks W H, Hunt W E, MacCarty C S, Mahaley M S Jr, Mealey J Jr, Owens G, Ransohoff J 2nd, Robertson J T, Shapiro W R, Smith K R Jr, Wilson C B, Strike T A. Randomized comparisons of radiotherapy and nitrosoureas for the treatment of malignant glioma after surgery. N Engl J. Med. 1980 Dec. 4; 303(23):1323-9.

Whiteman D C, Watt P, Purdie D M, Hughes M C, Hayward N K, Green A C. Melanocytic nevi, solar keratoses, and divergent pathways to cutaneous melanoma. J Natl Cancer Inst. Jun. 4 2003; 95(11):806-12.

Williams M L, Sagebiel R W. Melanoma risk factors and atypical moles. West J. Med. April 1994; 160(4):343-50.

Blask D E, Sauer L A, Dauchy R T et al. Melatonin inhibition of cancer growth in vivo involves suppression of tumor fatty acid metabolism via melatonin receptor-mediated signal transduction events. Cancer Res 1999; 59:4693-4701.

Xi S C, Siu S W, Fong S W et al. Inhibition of androgen-sensitive LNCaP prostate cancer growth in vivo by melatonin: association of antiproliferative action of the pineal hormone with mt1 receptor protein expression. Prostate 2001; 46:52-61.

Girgert R, Hanf V, Emons G, Grundker C. Membrane bound melatonin receptor MT1 down-regulates estrogen responsive genes in breast cancer cells. J Pineal Res 2009; 47:23-31.

Dauchy R T, Blask D E, Dauchy E M et al. Antineoplastic effects of melatonin on a rare malignancy of mesenchymal origin: melatonin receptor-mediated inhibition of signal transduction, linoleic acid metabolism and growth in tissue-isolated human leiomyosarcoma xenografts. J Pineal Res 2009; 47:32-42.

Cabrera J, Negrin G, Estevez F, Loro J, Reiter R J, Quintana J. Melatonin decreases cell proliferation and induces melanogenesis in human melanoma SK-MEL-1 cells. J Pineal Res. 2010 August; 49(1):45-54. Epub 2010 Apr. 29.

Hsieh T C, Wu J M. Resveratrol: Biological and pharmaceutical properties as anticancer molecule. Biofactors. 2010 September; 36(5):360-9.

Lee S J, Wang J Y. Exploiting the promiscuity of imatinib. J. Biol. 2009; 8(3):30. Epub 2009 Apr. 15.

Vella F, Ferry G, Delagrange P, Boutin J A. NRH:quinone reductase 2: an enzyme of surprises and mysteries. Biochem Pharmacol. 2005 Dec. 19; 71(1-2):1-12. Epub 2005 Oct. 25.

Werth V. Current treatment of cutaneous lupus erythematosus. Dermatol Online J. 2001 February; 7(1):2.

Youdim K A, Qaiser M Z, Begley D J, Rice-Evans C A, Abbott N J. Flavonoid permeability across an in situ model of the blood-brain barrier. Free Radic Biol Med. 2004 Mar. 1; 36(5):592-604.

Goodsell D S, Morris G M, Olson A J. Automated docking of flexible ligands: applications of AutoDock. J Mol. Recognit. 1996 January-February; 9(1):1-5.

Sussman J L, Abola E E, Lin D, Jiang J, Manning N O, Prilusky J. The protein data bank. Bridging the gap between the sequence and 3D structure world. Genetica. 1999; 106(1-2):149-58.

Fuhrmann J, Rurainski A, Lenhof H P, Neumann D. A new Lamarckian genetic algorithm for flexible ligand-receptor docking. J Comput Chem. 2010 Jul. 15; 31(9):1911-8.

Buryanovskyy L, Fu Y, Boyd M, Ma Y, Hsieh T C, Wu J M, Zhang Z. Crystal structure of quinone reductase 2 in complex with resveratrol. Biochemistry. 2004 Sep. 14; 43(36):11417-26.

What is claimed is:

1. A method for treating a patient with malignant glioma or thyroid cancer, the method comprising the step of administering to the patient a therapeutically effective amount of an oxazolidinone antibiotic, or a pharmaceutically acceptable salt thereof.

2. The method of claim 1 wherein the oxazolidinone antibiotic is a compound of formula (I)

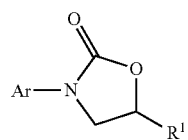

(I)

wherein Ar is an optionally substituted aryl or heteroaryl group and $R^1$ is an N-substituted amino(1-3C)alkyl group, a hydroxy(1-3C)alkyl group or a (5-membered-heteroaryl)oxy(1-3C)alkyl group.

3. The method of claim 2 wherein Ar is a group

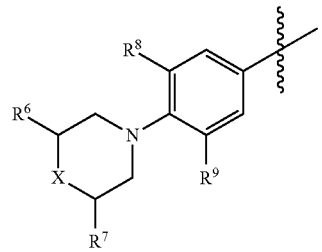

wherein X is O, S, SO, $SO_2$, $SNR^4$, $S(O)NR^4$, $NR^4$ or $NC(O)CH_2OR^4$, wherein $R^4$ is selected from hydrogen, $R^5$ and $C(O)R^5$ groups wherein $R^5$ is $(C_1-C_8)$ hydrocarbyl optionally substituted with one or more hydroxy, fluorine or chlorine groups; $R^6$ and $R^7$ are independently selected from hydrogen, methyl and cyano groups; and $R^8$ and $R^9$ are independently selected from hydrogen, fluorine and chlorine atoms.

4. The method of claim 2 wherein $R^1$ is a group $(CH_2)_nN(R^2)COR^3$, a group $(CH_2)_nOH$ or a group $(CH_2)_nOR^{10}$ wherein n is 1, 2 or 3, and $R^2$ and $R^3$ are independently selected from hydrogen and $(C_1-C_8)$ hydrocarbyl optionally substituted with one or more hydroxy, fluorine or chlorine groups and $R^{10}$ is a C-linked 5-membered heteroaryl ring containing 2 to 4 heteroatoms independently selected from N, O and S, which ring is optionally substituted on an available carbon atom by 1 or 2 substituents independently selected from $(C_1-C_4)$ alkyl, amino, $(C_1-C_4)$ alkylamino, $(C_1-C_4)$ alkoxy and halo, and/or on an available nitrogen atom, provided the ring is not thereby quaternized, by $(C_1-C_4)$ alkyl.

5. The method of claim 1 wherein the oxazolidinone antibiotic is (S)—N-[[3-[3-fluoro-4-(4-morpholinyl)phenyl]-2-oxo-5-oxazolidinyl]methyl]acetamide, N-[(5 S)-[3-[[3-fluoro-4-[4-(2-fluoroethyl)-3-oxopiperazin-1-yl]phenyl]-2-oxooxazolidin-5-yl]methyl]acetamide, N-[[(5 S)-3-[4-(1,1-dioxido-4-thiomorpholinyl)-3,5-difluorophenyl]-2-oxo-5-oxazolidinyl]methyl]acetamide, (S)—N-[[3-[5-(4-pyridyl)pyrid-2-yl]-2-oxo-5-oxazolidinyl]methyl] acetamide, or (S)—N-[[3-[5-(3-pyridyl)thiophen-2-yl]-2-oxo-5-oxazolidinyl]methyl]acetamide, or a pharmaceutically acceptable salt of the foregoing.

6. The method of claim 1 wherein the oxazolidinone antibiotic is a compound of the formula

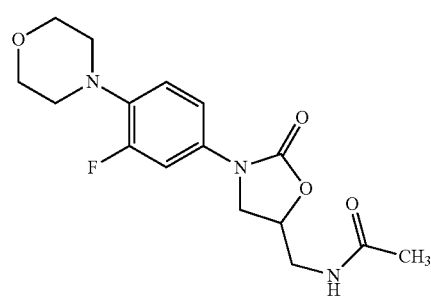 [SMILES: CC(=O)NCC1CN(c2ccc(N3CCOCC3)c(F)c2)C(=O)O1]

or a pharmaceutically acceptable salt thereof.

7. The method of claim 1 wherein the oxazolidinone antibiotic is a compound of the formula

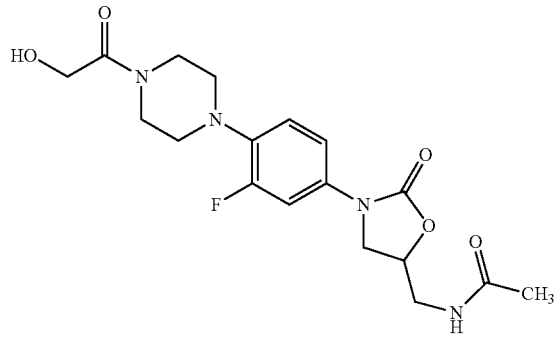 [SMILES: CC(=O)NCC1CN(c2ccc(N3CCN(C(=O)CO)CC3)c(F)c2)C(=O)O1]

or a pharmaceutically acceptable salt thereof.

8. The method of claim 1 wherein the oxazolidinone antibiotic is a compound of the formula

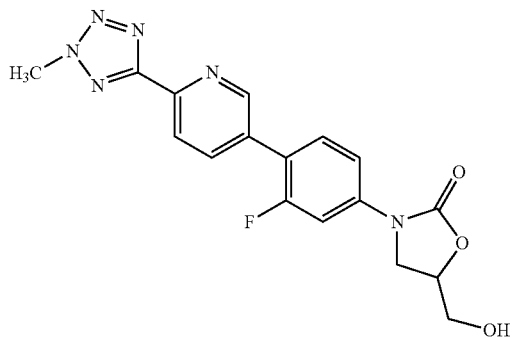 [SMILES: Cn1nnc(-c2ccc(-c3ccc(N4CC(CO)OC4=O)cc3F)cn2)n1]

or a pharmaceutically acceptable salt thereof.

9. The method of claim 1 wherein the oxazolidinone antibiotic is a compound of the formula

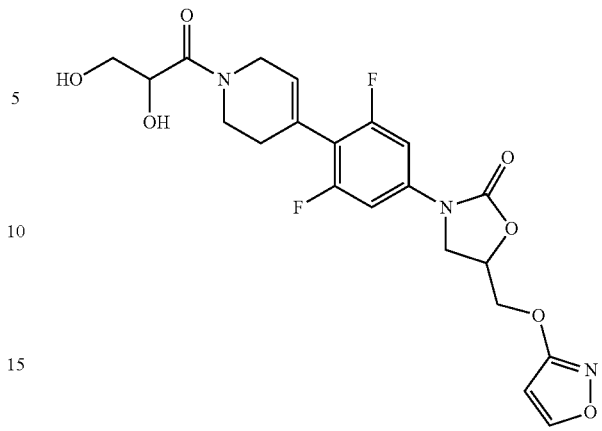

or a pharmaceutically acceptable salt thereof.

10. The method of claim 1 wherein the oxazolidinone antibiotic is administered in combination with an anti-cancer agent.

11. The method of claim 10 wherein the anti-cancer agent is selected from the group consisting of agomelatine, temozolomide, a corticosteroid, dacarbazine, carmustine, lomustine, vinblastine, vincristine, procarbazine, etoposide, irinotecan, bevacizumab, cetuximab, imatinib, gefitinib, erlotinib, tamoxifen, isotretinoin, thalidomide, vorinostat, bortezomib, interferon alpha-2b, and a platinum-containing drug, where the platinum-containing drug is selected from the group consisting of cisplatin, carboplatin, and oxaliplatin.

12. The method of claim 1 wherein the glioma is an astrocytoma, an oligodendroglioma, an oligoastrocytoma, or an ependymoma, or borderline form thereof.

13. The method of claim 1 wherein the oxazolidinone antibiotic is administered in combination with a therapeutically effective amount of an anti-cancer agent or in combination with a therapeutically effective amount of radiotherapy.

14. The method of claim 13 wherein the anti-cancer agent is agomelatine.

15. The method of claim 13 wherein the anti-cancer agent is temozolomide.

16. The method of claim 1 wherein the thyroid cancer is papillary, follicular, hurthle cell, medullary or anaplastic.

17. The method of claim 13 wherein the oxazolidinone antibiotic is administered in combination with a therapeutically effective amount of radiotherapy, delivered through external beam radiation, radioactive iodine, or a combination thereof.

* * * * *